(12) United States Patent
Hsieh et al.

(10) Patent No.: US 9,687,396 B2
(45) Date of Patent: Jun. 27, 2017

(54) ABSORBENT ARTICLE

(71) Applicant: HOMEWAY TECHNOLOGY CO., LTD., Tainan (TW)

(72) Inventors: Chin-Hsing Hsieh, Tainan (TW); Yi-Long Ho, Tainan (TW)

(73) Assignee: HOMEWAY TECHNOLOGY CO., LTD., Tainan (TW)

( * ) Notice: Subject to any disclaimer, the term of this patent is extended or adjusted under 35 U.S.C. 154(b) by 409 days.

(21) Appl. No.: 14/331,523

(22) Filed: Jul. 15, 2014

(65) Prior Publication Data

US 2015/0272791 A1 Oct. 1, 2015

(30) Foreign Application Priority Data

Mar. 27, 2014 (TW) .............. 103205299 U

(51) Int. Cl.
| | |
|---|---|
| *A61F 13/15* | (2006.01) |
| *A61F 13/20* | (2006.01) |
| *A61F 13/84* | (2006.01) |
| *A61F 13/551* | (2006.01) |
| *A61F 13/56* | (2006.01) |
| *A61F 13/472* | (2006.01) |

(52) U.S. Cl.
CPC .... *A61F 13/8405* (2013.01); *A61F 13/47263* (2013.01); *A61F 13/5514* (2013.01); *A61F 13/5611* (2013.01); *A61F 2013/8408* (2013.01); *A61F 2013/8414* (2013.01); *A61F 2013/8435* (2013.01)

(58) Field of Classification Search
CPC ....... A61F 13/5611; A61F 13/82; A61F 13/60
USPC .................................................... 604/385.05
See application file for complete search history.

(56) References Cited

U.S. PATENT DOCUMENTS

| | | | | |
|---|---|---|---|---|
| 3,665,922 A | * | 5/1972 | Skora .................. | A61F 13/4755 428/195.1 |
| 4,806,408 A | * | 2/1989 | Pierre ................ | A61F 13/4702 428/138 |
| 5,413,568 A | * | 5/1995 | Roach ................ | A61F 13/5514 206/440 |
| 5,458,592 A | * | 10/1995 | Abuto ................ | A61F 13/531 156/167 |
| 5,785,696 A | * | 7/1998 | Inoue ............... | A61F 13/53717 604/378 |
| 5,827,254 A | * | 10/1998 | Trombetta ............. | A61F 13/47 604/378 |
| 6,436,080 B1 | * | 8/2002 | Carlucci ............ | A61F 13/5146 428/154 |

(Continued)

FOREIGN PATENT DOCUMENTS

| | | |
|---|---|---|
| CN | 2704342 Y | 6/2005 |
| EP | 2415436 A1 | 2/2012 |

(Continued)

*Primary Examiner* — Michele M Kidwell
(74) *Attorney, Agent, or Firm* — Duane Morris LLP

(57) ABSTRACT

An absorbent article includes an absorbent core, a liquid impervious backsheet, a liquid pervious topsheet, a functional layer, an adhesive layer and a releasable film. The functional layer includes a plurality of functional particles that are made from a material selected from sodium carbonate, argireline, mineral rock crystal, porphyritic andesite, borneol, mint essential oil, eucalyptus essential oil, jasmine essential oil, far-infrared radiation particles and combinations thereof.

10 Claims, 4 Drawing Sheets

(56) References Cited

U.S. PATENT DOCUMENTS

| | | | |
|---|---|---|---|
| 6,710,225 B1* | 3/2004 | Everett | H01L 27/115 |
| | | | 257/E21.69 |
| 6,770,064 B1 | 8/2004 | Ruscher | |
| 6,838,591 B2* | 1/2005 | Waksmundzki | A61F 13/53743 |
| | | | 604/378 |
| 8,975,466 B2* | 3/2015 | Marcelo | A61F 13/4756 |
| | | | 604/378 |
| 9,592,316 B2* | 3/2017 | Ichihara | A61F 13/42 |
| 2003/0135177 A1* | 7/2003 | Baker | A61F 13/15634 |
| | | | 604/368 |
| 2003/0211248 A1* | 11/2003 | Ko | A61F 13/15658 |
| | | | 427/385.5 |
| 2007/0049892 A1* | 3/2007 | Lord | A61F 13/531 |
| | | | 604/385.16 |
| 2007/0093770 A1* | 4/2007 | Ecker | A61F 13/475 |
| | | | 604/385.01 |
| 2007/0219515 A1* | 9/2007 | Marsh | A61F 13/8405 |
| | | | 604/359 |
| 2009/0112173 A1* | 4/2009 | Bissah | A61F 13/536 |
| | | | 604/378 |
| 2011/0208147 A1* | 8/2011 | Kawakami | A61F 13/5323 |
| | | | 604/372 |

FOREIGN PATENT DOCUMENTS

| | | |
|---|---|---|
| JP | 2000-217860 A | 8/2000 |
| WO | 2007/091751 A1 | 8/2007 |

* cited by examiner

ABSORBENT ARTICLE

CROSS-REFERENCE TO RELATED APPLICATION

This application claims priority of Taiwanese Patent Application No. 103205299, filed on Mar. 27, 2014, the entire disclosure of which is hereby incorporated by reference.

BACKGROUND OF THE INVENTION

1. Field of the Invention

This invention relates to an absorbent article, more particularly to a sanitary napkin.

2. Description of the Related Art

A sanitary napkin is an indispensable product for women in the period of menstruating. The sanitary napkin is designed to absorb body exudate and to avoid leakage of the exudate. However, in use, the sanitary napkin tightly contacts the user's skin so as to create a wet, hot, and unventilated environment therebetween, which is a hotbed for microorganisms, thereby resuming in microbial infection, itching, and other symptoms. Moreover, bad odor is also likely to be produced.

SUMMARY OF THE INVENTION

Therefore, the object of the present invention is to provide an absorbent article that can overcome the aforesaid drawbacks of the prior art.

According to this invention, an absorbent article includes a main body that includes an absorbent core, a liquid impervious backsheet, a liquid pervious topsheet, a functional layer, an adhesive, layer and a releasable film. The absorbent core includes a plurality of polymeric particles. The liquid impervious backsheet is disposed on the absorbent core. The liquid pervious topsheet is disposed on the absorbent core oppositely of the liquid impervious backsheet and is connected to the liquid impervious backsheet. The functional layer is disposed between the liquid pervious topsheet and the absorbent core, and includes a plurality of functional particles. The functional particles of the functional layer are made from a material selected from the group consisting of sodium carbonate, argireline, mineral rock crystal, porphyritic andesite, borneol, mint essential oil, eucalyptus essential oil, jasmine essential oil, far-infrared radiation particles and combinations thereof. The adhesive layer is disposed on the liquid impervious backsheet oppositely of the topsheet. The releasable film is detachably affixed to the adhesive layer oppositely of the liquid impervious backsheet.

BRIEF DESCRIPTION OF THE DRAWINGS

Other features and advantages of the present invention will become apparent in the following detailed description of the preferred embodiment of this invention, with reference to the accompanying drawings, in which.

DETAILED DESCRIPTION OF THE PREFERRED EMBODIMENTS

Figure 1:
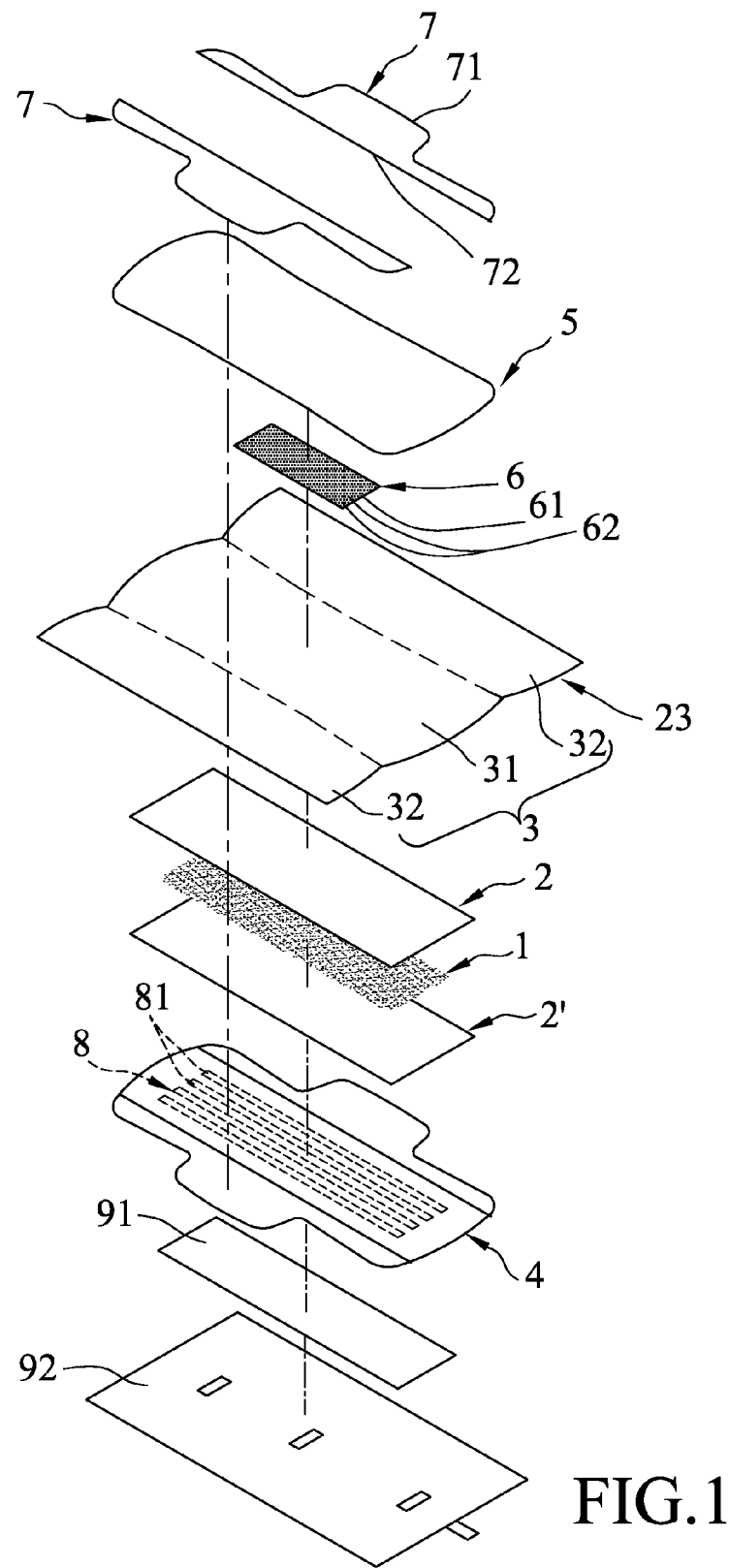
FIG. 1 is an exploded perspective view of the preferred embodiment of an absorbent article according to this invention.
Figure 2:
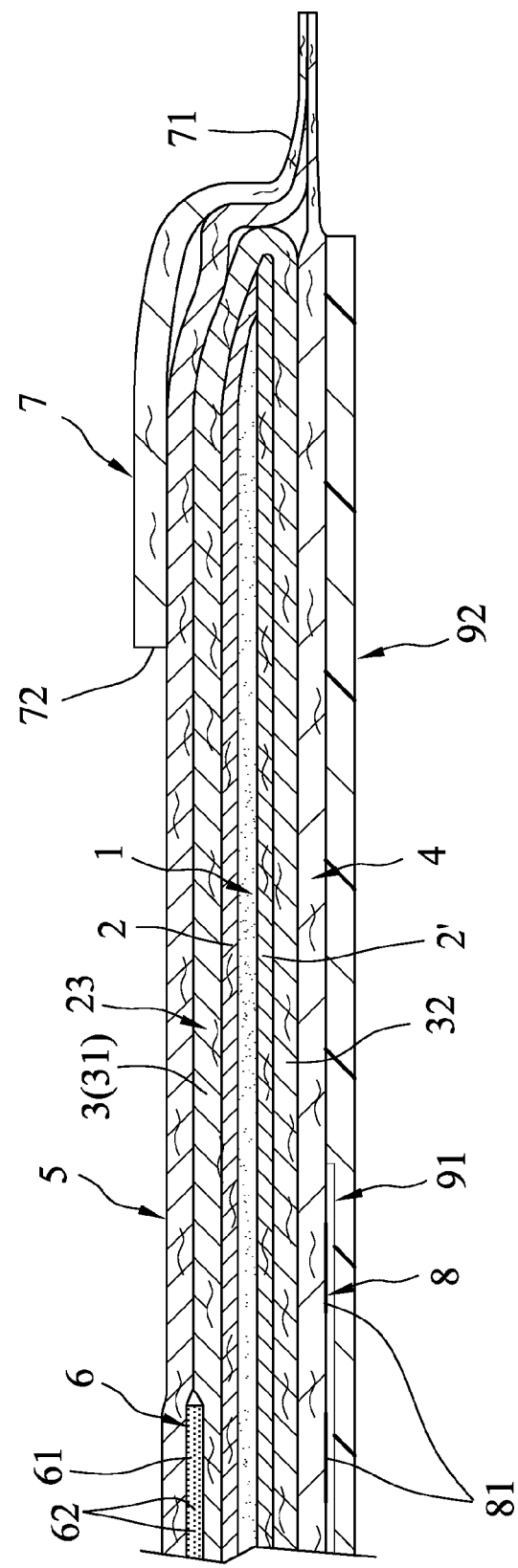
FIG. 2 is a fragmentary sectional view of the preferred embodiment.
Figure 3:
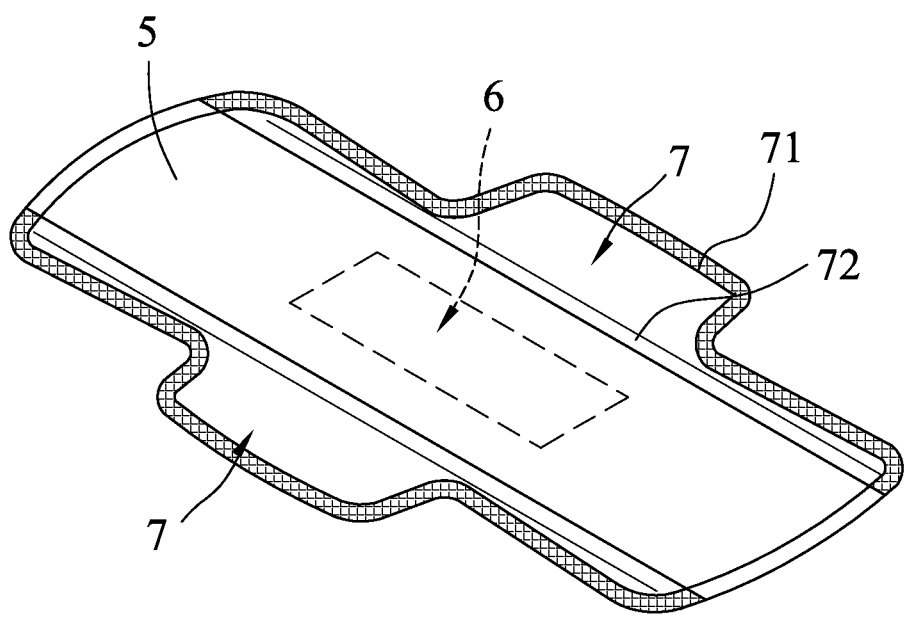
FIG. 3 is a perspective view of the preferred embodiment in an unfolded state.
Figure 4:
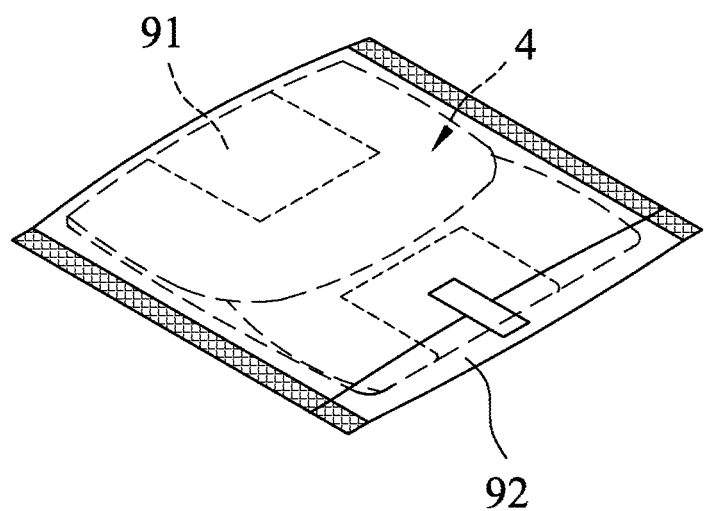
FIG. 4 shows the preferred embodiment in a folded state.

Referring to FIGS. 1 to 4, the preferred embodiment of an absorbent article according to the present invention is shown to include a main body that includes an absorbent core 1, a liquid impervious backsheet 4, a liquid pervious topsheet 5, a functional layer 6, an adhesive layer 8 and a releasable film 91.

The absorbent core 1 includes a plurality of polymeric particles having good water-absorption property so as to absorb water quickly and to keep the liquid pervious topsheet 5 of the absorbent article dry. Preferably, the absorbent core 1 has a thickness ranging between 1.1 and 1.3 mm. In this embodiment, the absorbent core 1 has a thickness of 1.2 mm.

The liquid impervious backsheet 4 is disposed on the absorbent core 1 and is made from a waterproof and air-permeable material. Preferably, the liquid impervious backsheet 4 has a thickness ranging between 0.2 and 0.4 mm, and a basis weight ranging between 25 and 45 $g/m^2$. In this embodiment, the liquid impervious backsheet 4 has a thickness of 0.3 mm and a basis weight of 35 $g/m^2$.

The liquid pervious topsheet 5 is disposed on the absorbent core 1 oppositely of the liquid impervious backsheet 4, is connected to the liquid impervious backsheet 4, and is adapted for contact with a user's skin. The liquid pervious topsheet 5 is made of a water-absorbing, a air-permeable and soft material. Preferably, the liquid pervious topsheet 5 has a thickness ranging between 0.4 and 0.6 mm, and a basis weight ranging between 1.5 and 35 $g/m^2$. In this embodiment, the liquid pervious topsheet 5 is made of nonwoven fabric and has a thickness of 0.5 mm and a basis weight of 25 $g/m^2$.

The functional layer 6 is disposed between the liquid pervious topsheet 5 and the absorbent core 1, and includes a substrate 61 and a plurality of functional particles 62 distributed over the substrate 61. The functional particles 62 are made from a material selected from the group consisting of sodium carbonate, argireline, mineral rock crystal from deep ocean, porphyritic andesite, borneol, mint essential oil, eucalyptus essential oil, jasmine essential oil, far-infrared radiation particles and combinations thereof.

Sodium carbonate ($Na_2CO_3$) is an anhydrous sodium salt of carbonic acid, and is used in textile washing, cleaning, chemical, and pharmaceutical industries. In this embodiment, sodium carbonate is to improve the absorbence of the absorbent article.

Argireline is an antiager and used to improve the skin quality.

Mineral rock crystal is obtained from metamorphic rocks which are formed through transformation of protoliths attributed to heat or pressure. The mineral rock crystal has an irregular and porous structure, and the porous structure can be used no adsorb bacteria.

Porphyritic andesite contains aluminosilicates (feldspar) which are capable of adsorbing bacteria and pigments. The adsorbing ability of porphyritic andesite could be improved if porphyritic andesite is in powder form. When porphyritic andesite is placed in water, it is capable of adsorbing ions that are dissolved in water and then releases micro-elements (for example, K, Ca, Mg, Si, Fe, Zn, Cu, Mo, Se, Mn, Sr, Ni, V, Li, Co, Cr, I, Ge, Ti and etc.). Moreover, the porphyritic andesite can also release amino acid that is essential to the human body. Porphyritic andesite is a kind of quartz porphyry in volcanic rock. It is capable of treating dermatosis, swelling, mange and etc. Moreover, porphyritic andesite contains a large amount of zircon that is capable of releasing infrared ray and is good for the human body.

Natural borneol is made from *Dryobalanops aromatica Gaertn.* f., and is also known as camphol. Alternatively, natural borneol can be made from *Bliamea balsamifera* DC., and is known as nagi-camphor. Nowadays, borneol is often made from turpentine oil and camphor using chemical synthesis. Natural borneol has cold property and can be used for refreshment, analgesia, detoxification, detumescence, and antisepsis. It also exhibits inhibition effect on *Staphylococcus, Streptococcus, Diplococcus pneumoniae, Escherichia coli* and etc. It also has a slight stimulation effect and thus provides mild analgesia effect.

Mint essential oil is made from peppermint. Peppermint contains menthol that has abilities of contraction of capillary, refreshment, deodorization, and easement of eczema, itching, inflammation, and burns. It is also good for oily hair and skin. When used in the absorbent article of this invention, menthol would provide nice and cool, smell and feeling for 90 to 120 minutes under a temperature above 30° C. In this embodiment, mint essential oil is an India mint essential oil.

Eucalyptus essential oil has abilities of sterilization effect on bacteria and virus and relaxation of mucosa.

Jasmine essential oil can soothe nerve tension, make people feel refreshed and optimistic, enhance uterine contraction and blood flowing rate, improve skin elasticity, treat scars and ease pain. It is suitable for dry, oily and sensitive skin.

Far-infrared radiation particles emit far-infrared radiation having a wavelength ranging between 15 μm and 1 mm. It has been proven in clinical trials that the far-infrared radiation has strong permeability and is able to penetrate 5 to 10 cm beneath human skin. The infrared radiation has effects on activation of cells, improvement of blood circulation, acceleration of metabolism, deodorization, and anti-bacteria, and thus can ease discomfort caused by dysmenorrheal.

The adhesive layer 8 is disposed on lee liquid impervious backsheet 4 oppositely of the topsheet 5 for adhesion of the absorbent article to a user's undergarment. In this embodiment, the adhesive layer 8 includes a plurality of strip portions 81 spaced apart from and parallel to each other. The adhesive layer 8 is made of, for example but not limited to, fluorescence-exclusive hot melt adhesive commercially available from Henkel company.

The releasable film 91 is detachably affixed to the adhesive layer 8 oppositely of the liquid impervious backsheet 4 for protection of the adhesive layer 8. Preferably, the releasable film 91 has a thickness ranging between 0.2 and 0.4 mm, and a basis weight ranging between 32 and 52 g/m². In this embodiment, the releasable film 91 is made of a release paper that is made from natural wood pulp, and has a thickness of 0.3 mm and a basis weight of 42 g/m².

The main body further includes an enclosing layer 23 enclosing the absorbent core 1 and including top and bottom sub-layers 2,2' that are disposed on opposite top and bottom surfaces of the absorbent core 1, and a surrounding sub-layer 3 that surrounds the top and bottom sub-layers 2,2'. The surrounding sub-layer 3 has a middle portion 31 covering the top sub-layer 2 of the enclosing layer 23, and two folded-back portions 32 connected to two longitudinal edges of the middle portion 31 and folded back to cooperatively cover the bottom sub-layer 2'. The enclosing layer 23 is a paper that is made from natural wood pulp. In this embodiment, the enclosing layer 23 is made of an airlaid paper which is soft and has good water absorption and good elasticity. Preferably, each of the top and bottom sub-layers 2,2' and the surrounding sub-layer 3 has a thickness ranging between 0.7 and 0.9 mm, and a basis weight ranging between 50 and 60 g/m², In this embodiment, each of the top and bottom sub-layers 2,2' and the surrounding sub-layer 3 has a thickness of 0.8 mm and a basis weight of 60 g/m².

The main body has two spaced-apart longitudinal edges. The absorbent article further includes two flaps 7 respectively connected to the longitudinal edges of the main body. Each of the flaps 7 has an outer edge 71 that is away from the other one of the flaps 7 and that is connected to the liquid pervious topsheet 5 and the liquid impervious backsheet 4 using thermal pressing, and an inner edge 72 that is adjacent to the other one of the flaps 7 and that is detachably disposed on the liquid pervious topsheet 5 to prevent liquid from leaking from the longitudinal edges of the main body. The flaps 7 are made of a soft, water-absorbent and air-permeable material.

The absorbent article further includes a releasable wrapper 92. When the main body (or the main body along with the flaps 7) is/are in a folded state, the releasable wrapper 92 covers the main body (or the main body along with the flaps 7) for protection of the main body against exposure to external environment before use. The releasable wrapper 92 is made of a waterproof and soft material, for example but not limited to, a casting film. In this embodiment, the releasable wrapper 92 is affixed to the releasable film 91 of the main body so that, in use, the releasable wrapper 92 and the releasable film 91 can be torn of from the liquid impervious backsheet 4 together. Preferably, the releasable wrapper 92 has a thickness ranging between 0.2 and 0.4 mm, and a basis weight ranging between 15 and 35 g/m². In this embodiment, the releasable wrapper 92 has a thickness of 0.3 mm and a basis weight of 25 g/m².

Preferably, the absorbent article is a sanitary napkin.

In use, the releasable wrapper 92 along with the releasable film 91 is torn off from the liquid impervious backsheet 4. The main body of the absorbent article is thus turned from a folded state (see FIG. 4) into an un-folded state. The liquid impervious backsheet 4 of the main body is then adhered to a user's undergarment via the adhesive layer 8. The liquid pervious topsheet 5 contacts the user's body so that the absorbent core 1, the liquid pervious topsheet 5 and the enclosing layer 23 are able to absorb body exudate, e.g., blood, urine, etc. The flaps 7 prevent leakage of the body exudate. The functional particles 62 of the functional layer 6 have anti-bacterial, anti-inflammatory and deodorization effects, and may prevent various gynecological diseases caused by bacterial infection.

While the present invention has been described in connection with what is considered the most practical and preferred embodiment, it is understood that this invention is not limited to the disclosed embodiment but is intended to cover various arrangements included within the spirit and scope of the broadest interpretation and equivalent arrangements.

What is claimed is:

1. An absorbent article, comprising:
   a main body that has two spaced-apart longitudinal edges and comprises:
      an absorbent core including a plurality of polymeric particles,
      an enclosing layer that encloses said absorbent core and that includes top and bottom sub-layers disposed on opposite top and bottom surfaces of said absorbent core, and a surrounding sub-layer surrounding said top and bottom sub-layers, said surrounding sub-layer having a continuous and seamless middle portion covering said top sub-layer of said enclosing layer, and two folded-back portions connected to two longitudinal edges of said middle portion and folded back to cooperatively cover said bottom sub-layer of said enclosing layer, a liquid impervious backsheet disposed on said absorbent core, a liquid pervious topsheet disposed on said absorbent core oppositely of said liquid impervious backsheet and being connected to said liquid impervious backsheet, an adhesive layer disposed on said liquid impervious backsheet oppositely of said liquid pervious topsheet, a releasable film detachably affixed to said adhesive layer oppositely of said liquid impervious backsheet, and a functional layer disposed between said liquid pervious topsheet and said absorbent core, and including a plurality of functional particles which are made from a material selected from the group consisting of sodium carbonate, argireline, mineral rock crystal, porphyritic andesite, borneol, mint essential oil, eucalyptus essential oil, jasmine essential oil, far-infrared radiation particles and combinations thereof; and two flaps respectively connected to said longitudinal edges of said main body, each of said flaps having an outer edge that is away from the other one of said flaps and that is connected to said liquid pervious topsheet and said liquid impervious backsheet, and an inner edge that is adjacent to the other one of said flaps and that is detachably disposed on said liquid pervious topsheet.

2. The absorbent article as claimed in claim 1, wherein said enclosing layer is made of paper.

3. The absorbent article as claimed in claim 1, wherein each of said top and bottom sub-layers and said surrounding sub-layer has a thickness ranging between 0.7 and 0.9 mm and a basis weight ranging between 50 and 60 g/m².

4. The absorbent article as claimed in claim 1, further comprising a releasable wrapper, wherein, when said main body is in a folded state, said releasable wrapper covers said main body for protection of said main body against exposure to external environment.

5. The absorbent article as claimed in claim 4, wherein said releasable wrapper is made of a casting film and has a thickness ranging between 0.2 and 0.4 mm and a basis weight ranging between 15 and 35 g/m².

6. The absorbent article as claimed in claim 1, wherein said absorbent core has a thickness ranging between 1.1 and 1.3 mm.

7. The absorbent article as claimed in claim 1, wherein said liquid impervious backsheet has a thickness ranging between 0.2 and 0.4 mm and a basis weight ranging between 25 and 45 g/m².

8. The absorbent article as claimed in claim 1, wherein said liquid pervious topsheet has a thickness ranging between 0.4 and 0.6 mm and a basis weight ranging between 15 and 35 g/m².

9. The absorbent article as claimed in claim 1, wherein said releasable film is made of a release paper and has a thickness ranging between 0.2 and 0.4 mm and a basis weight ranging between 32 and 52 g/m².

10. The absorbent article as claimed in claim 1, which is a sanitary napkin.

* * * * *